United States Patent [19]
Murad

[11] Patent Number: 5,804,168
[45] Date of Patent: Sep. 8, 1998

[54] PHARMACEUTICAL COMPOSITIONS AND METHODS FOR PROTECTING AND TREATING SUN DAMAGED SKIN

[76] Inventor: Howard Murad, 4316 Marina City Dr., Marina del Rey, Calif. 90292

[21] Appl. No.: 790,190

[22] Filed: Jan. 29, 1997

[51] Int. Cl.$^6$ .............................. A61K 7/42; A61K 7/44; A61K 7/00
[52] U.S. Cl. ............................. 424/59; 424/60; 424/400; 424/401
[58] Field of Search ............................... 424/59, 60, 400, 424/401

[56] References Cited

U.S. PATENT DOCUMENTS

| | | | |
|---|---|---|---|
| 5,290,605 | 3/1994 | Shapira | 424/439 |
| 5,364,617 | 11/1994 | Bush et al. | 424/59 |

OTHER PUBLICATIONS

Medline Abs., Todd, S., et al., "An investigation of the relationship between antioxidant vitamin intake and coronary heart disease in men and women using logistic regression analysis", *J. of Clinical Epidemiology*, 48(2):307–16 (1995).

Medline Abs., Nachbar, F., et al., "The role of vitamin E in normal and damged skin", *J. of Molecular Medicine*, 73(1):7–17 (1995).

Medline Abs., Maitra, I., et al., "Peroxyl radical scavenging activity of Ginkgo Biloba extract EGb 761", *Biochemical Pharmacology*, 49(11):1649–55 (1995).

Medline Abs., Grimble, R.F., "Nutritional antioxidants and the modulation of inflammation: theory and Practice", *New Horizons*, 2(2):175–85 (1994).

Medline Abs., Maffei, F., et al., "Free radicals scavenging action and anti–enzyme activities of procyandines from *Vitis vinifera*. A mechanism for their capillary action", *Arznei-mittel–Forschung*, 44(5):592–601 (1994).

Medline Abs., Oyama, Y., et al., "Myricetin and quercetin, the flavonoid constituents of Ginkgo Biloba extract greatly reduce oxidative metabolism in both resting and Ca(2+)–loaded brain neurons", *Brain Research*, 635(1–2):125–9 (1994).

Medline Abs., Paranich, A.V., et al., "Effect of supposed radioprotectors on oxidation–reduction of vitamin E in the tissues of irradiated rats", *Radiats Biol Radioecol (Russia)*, 33(5)653–7 (1993).

Medline Abs., Bukovsky, M., et al., "Testing for immunomodulating effects of ethanol–water extracts of the above–ground parts of the plants Echinaceae (Moench) and Rudbeckia L.", *Ceskoslovenska Farmacie*, 42(5):228–31 (1993).

Medline Abs., Xie, B., et al., "Antioxidant properties of fractions and polyphenol constituents from green, oolong and black teas", *Life Sciences*, 17(2):77–84 (1993).

Medline Abs., Dowling, E.J. et al., "Assessment of a human recombinant manganese superoxide dismutase in models of inflammation", *Free Radical Research Communications*, 18(5):291–8 (1993).

Medline Abs., Deucher, G.P., "Antioxidant therapy in the aging process", 62:428–37 (1992).

Medline Abs., Zafirov, D., et al., "Antiexudative and capillaritonic effects of procyanidines isolatred from grape seeds (V. Vinifera)", *Acta Physiologica et Pharmacologica Bulgarica*, 16(3):50–4 (1990).

D. Mowery, *The Scientific Validation of Herbal Medicine*, 247–251 (1986).

M. Tierra, *Planetary Herbology*, p. 194 (1988).

G. La Ruche & J.P. Cesarini, "Protective effect of oral selenium plus copper associated with vitamin complex on sunburn cell formation in human skin," *Photodermal Photoimmunol Photomed.*, 8:232–235 (1991).

P. Pugliese, "A Brief Introduction to Free Radicals and Oxygen Stress," Paper presented at International Conference of Aesthetics and Dermatology, Los Angeles (Feb. 1991).

P. Mayer, et al., "The Effects of Vitamin E on the Skin," *Cosmetics & Toiletries*, 108:99–109 (Feb. 1993).

K. Werninghaus, et al., "Evaluation of the Photoprotective Effect of Oral Vitamin E Supplementation," *Arch. Dermatol.*, 130:1257–1261 (Oct. 1994).

R. Facino, et al., "Echinacoside and caffeoyl conjugates protect collagen from free radical–induced degradation: a potential use of Echinecea extracts in the prevention of skin photodamage," *Planta Med.*, 61:510–514 (1995).

J. Weiss, "Sun Damage & Photoaging," *Skin*, 16–23 (Mar./Apr. 1996).

H. Lim & J. Epstein, "Photosensitivity Diseases," *J. Am. Acad. Dermatol.*, 36:84–90 (1997).

*Primary Examiner*—Shelley A. Dodson
*Attorney, Agent, or Firm*—Pennie & Edmonds LLP

[57] ABSTRACT

This invention relates to a pharmaceutical composition for the protection and prevention of skin damage to a patient resulting from exposure to sunlight having at least one antioxidant component in an amount sufficient to inhibit the formation of free radicals; at least one anti-inflammatory component in an amount sufficient to substantially inhibit the inflammation associated with exposure to sunlight; and at least one immunity boosting component to enhance the patient's immune response. In a preferred form, the composition also includes a cysteine component, a magnesium component, a manganese component, a copper component, a selenium component, and a carotenoid component. In a more preferred form the invention also includes wild yam root, wild yam extract, yellow dock, bupleurum, poria cocos, gentian root, myrrh gum, hawthorn berry extract, and rosemary extract. The invention also relates to a method for protecting skin from damage caused by exposure to sunlight by administering the pharmaceutical composition in an amount therapeutically effective in increasing the sun protection factor of the skin.

21 Claims, No Drawings

PHARMACEUTICAL COMPOSITIONS AND METHODS FOR PROTECTING AND TREATING SUN DAMAGED SKIN

TECHNICAL FIELD

This invention relates to pharmaceutical compositions, as well as methods, to protect skin from the armful effects of sunlight.

BACKGROUND OF THE INVENTION

The skin is the most environmentally-stressed organ in mammals, particularly in humans. Not only is the skin subjected to toxic chemicals and hostile environments, but it also is the only organ directly exposed to Ultraviolet ("UV") light in the presence of oxygen. [See, e.g., P. Mayer, et al., *Cosmetic & Toiletries*, 108:99–109 (February 1993)]. Lengthy exposure of the skin to UV light typically damages the skin, resulting, in sunburn, photoaging and carcinogenesis.

UV light exposure in the presence of oxygen results in the creation of free radicals. In the skin, these radicals frequently trigger the release of inflammatory mediators, commonly manifested as sun burn; cytoskeletal alterations, breaking down the collagen in the skin; and may also result in structural DNA changes, such as DNA strand breaks and dimer formation. [K. Werninghaus, et al., *Arch Dermatol.*, 130:1257–1261 (October 1994)]. The body attempts to neutralize the free radicals generated by UV light through the use of antioxidants. Antioxidants are commonly found in two forms-enzymatic and non-enzymatic. Superoxide dismutase (SOD), catalase, and glutathione peroxidase are natural enzymatic antioxidants used by the body. SOD accelerates the spontaneous reduction of superoxide free radicals into peroxides and oxygen. Catalase then further decomposes hydrogen peroxide into water and oxygen. Finally, the glutathione peroxidase reduces both hydrogen peroxide and free organic hydroperoxides. Non-enzymatic antioxidants, such as Vitamin E (tocopherol), Vitamin A (beta-carotene), and Vitamin C (ascorbic acid) have been individually applied to assist the skin in scavenging free radicals and neutralizing the harmful effects of UV light. [P. Pugliese, "A Brief Introduction to Free Radicals and Oxygen Stress," Paper presented at International Conference of Aesthetics and Dermatology, Los Angeles, (February 1991)]. Conventional skin protection efforts typically attempt to either shield the skin from UV light to prevent the production of free radicals, or provide additional agents capable of neutralizing the free radicals.

Topical applications are one such effort well known in the art that shields the skin from the sun's harmful effects. These sun-screens often are water- or oil-based lotions or ointments that incorporate photo-protectant materials such as titanium and zinc oxide. [J. Weiss, *Skin*, 16–23 (March/April 1996)]. Although the most widely used form of protection against exposure to sunlight, these topical applications suffer from several drawbacks. First, large amounts of photo-protective materials are incorporated into the topical applications, some of which have recently become suspect of having toxicity under these conditions or otherwise being harmful. Furthermore, the effectiveness of such topical applications is dependent upon a constant and uniform coverage of the skin, which is often difficult to obtain. Many individuals fail to use these topical sunscreens on a regular or continuing basis, as is required under prolonged UV exposure. Finally, sunscreens do not provide good protection for all types of UV light. [Id.].

In addition, various conventional supplements have attempted to boost the body's natural antioxidant activity using vitamins, minerals, and herbs. Vitamin C, for example, is believed to reduce sun damage, and vitamin E has been used topically as an anti-inflammatory agent and for UV-ray protection of cells. Also, carotenoids may have usefulness as antioxidants, protecting against both free radicals and singlet oxygen, a highly reactive, diamagnetic excited state of dioxygen. Moreover, it is thought that minerals are typically needed to maintain the effectiveness of the body's enzymatic antioxidants. Both copper and zinc are thought to be necessary in the proper functioning of SOD. [G. La Ruche & J.-P. Cesarini, *Photodermatol Photoimmunol Photomed.*, 8:232–235 (1991)]. Manganese is believed to be a cofactor in the mitochondrial form of SOD. Also, selenium is thought to be necessary to glutathione peroxidase, an important antioxidant found naturally in the body. Unfortunately, few experiments into the skin-protecting effects of these antioxidants have provided conclusive results.

In particular, a study that orally administered vitamin E supplements to participants and then tested their response to the sun found that Vitamin E did not mitigate the UV damage, despite the fact that the subjects were given thirteen times the recommended daily allowance. [K. Werninghaus, et al., *Arch. Dermatol.*, 130:1257–1261 (October 1994)]. Furthermore, beta-carotene has been reported to have beneficial effects in some studies, but has had no effect in others. Finally, another study noted the photo-protective effect of the oral administration of butylated hydroxy toluene, but little effect was shown using vitamins C or E.

Certain herbs have also been found helpful in protecting the skin from the sun's harmful effects. Herb extracts such as burdock root, echinacea, yellow dock root and grape seeds posses detoxifying properties that have been individually applied to help the body eliminate harmful free radicals. Burdock root contains the active ingredient inulin, and is useful in treating cankerous skin conditions, as well as inflammation. Echinacoside and caffeoyl derivatives present in echinacea act as potent antioxidants, which protect the skin when applied topically. [R. Facino, et al., *Planta Med.* 61:510–514 (1995)]. Yellow dock root contains the active constituent chrysarobin, which has been used in the treatment of chronic skin diseases, such as eczema, leprosy, psoriasis, and cancer. [M. Tierra, "Planetary Herbology," p. 194 (1988)]. Potent bioflavanoids, known as oligomeric proanthocyanidins (OPC's), are found in grape seeds. These OPC's are thought to be potent antioxidants possessing 20 times the antioxidant power of vitamin C and 50 times the antioxidant power of vitamin E. These herbs have been individually used both topically and orally to protect the skin from various afflictions.

Other studies have attempted to demonstrate the synergistic effect of a mixture of antioxidants. In one study, the subjects were given selenium and copper along with a vitamin supplement of vitamin A and E. [G. La Ruche & J. P. Cesarini, *Photodermatol Photoimmunol Photomed.*, 8:232–235 (1991)]. Although the supplements did protect the skin cells to some extent against ultraviolet-induced cell damage, they did not prevent light-induced erythema, redness.

Also, U.S. Pat. No. 5,290,605, discloses a soft drink that provides protection against sun damage. This drink contains a mixture of carotenoids, optionally together with vitamin C, vitamin E, or other effective antioxidants. The above antioxidants are limited to an amount which does not exceed ten vitamin A RDA equivalents of provitamin A per liter of drink.

Nutritional supplements such as Source Naturals' PYCNOGENOL® COMPLEX™ provide a variety of vitamins, minerals and herb extracts to protect the body against free radicals. In particular, the PYCNOGENOL® COMPLEX™ contains pycnogenol, proanthodyn, quercetin, Ginkgo Biloba extract, Green Tea extract, Bilberry extract, Silymarin, Tumeric extract, Hawthorn Berry extract, Rosemary extract, vitamin C (in the form of zinc and magnesium ascorbates), and magnesium.

Also, an herbal supplement and nutritional suggestions for the maintenance of the skin are disclosed in "The Scientific Validation of Herbal Medicine" by Daniel B. Mowrey, Ph.D. (p.247–251 1986). The herbal supplement consists of extracts of chaparral, dandelion root, burdock root, licorice root, echinacea, yellow dock root, kelp and cayenne. The reference also suggests the use of the following nutritional supplements: vitamin A, vitamin $B_1$, vitamin $B_2$, vitamin $B_6$, a vitamin B complex, vitamin C, vitamin D, vitamin E, niacinamide, pantothenic acid, para-aminobenzoic acid, biotin, choline, inositol, folic acid, zinc, calcium, magnesium, and potassium.

Although the above supplements and studies provide UV-protection for the skin, none provide for all aspects of an antioxidant supplement necessary to protect the skin from damage resulting from exposure to sunlight. It is desired that a composition be formulated that contains the proper ratio of vitamins, minerals and herbal components to more effectively and advantageously provide protection to the sun or other sources of UV-damage.

SUMMARY OF THE INVENTION

The invention relates to a pharmaceutical composition for the prevention and treatment of skin damage resulting from exposure to light in a patient. The pharmaceutical composition has at least one primary antioxidant component in an amount sufficient to reduce free radicals; at least one anti-inflammatory component in an amount sufficient to reduce inflammation of the skin; and at least one immunity boosting component in an amount sufficient to enhance the patient's immune response to prevent or facilitate repair of damaged skin.

In a preferred embodiment, the primary antioxidant component is present in about 5 to 50 weight percent, the anti-inflammatory component is present in about 5 to 40 weight percent, and the immunity boosting component is present in about 1 to 20 weight percent of the composition.

In one embodiment, the primary antioxidant component comprises at least one of a catechin-based preparation, a vitamin A source, a ginkgo biloba extract, a silymarin source, a quercetin compound, and a vitamin C source.

In a preferred embodiment, the primary antioxidant component comprises at least a proanthanol or proanthocyanidin as the catechin-based preparation, vitamin A palmitate as the vitamin A source, milk thistle extract as the silymarin source, quercetin dihydrate as the quercetin compound, and an ascorbic acid compound or a salt or ester thereof as the vitamin C source.

In a more preferred embodiment, the primary antioxidant component comprises proanthocyanidin present in about 0.1 to 5 weight percent, vitamin A palmitate present in about 0.1 to 5 weight percent, ginkgo biloba extract present in about 0.01 to 3 weight percent, quercetin dihydrate present in about 1 to 20 weight percent, ascorbic acid present in about 5 to 50 weight percent, and milk thistle extract present in about 1 to 20 weight percent.

In another embodiment, the anti-inflammatory component comprises a vitamin E source, a zinc compound or a pharmaceutically acceptable salt thereof.

In a preferred embodiment, the vitamin E source is a sulfate or succinate complex of vitamin E and the zinc compound is a complex of zinc and an amino acid. In a more preferred embodiment, the vitamin E source is D-alpha tocopherol acid succinate present in about 5 to 40 weight percent, and the zinc compound is zinc monomethinone present in about 1 to 12 weight percent, wherein the zinc is preferably present in about 10 to 30 weight percent of the complex.

In another embodiment, the immunity boosting component comprises at least one of echinacea, an echinacea extract, and golden seal.

In one embodiment, the composition further comprises a pharmaceutically acceptable carrier or excipient.

In yet another embodiment, the pharmaceutical composition further has one or more of a cysteine component, a magnesium component, manganese component, a copper component, a selenium component, or a carotenoid component.

In a preferred embodiment, the cysteine component is N-acetyl cysteine and is present in about 1 to 10 weight percent, the magnesium component is magnesium ascorbate and is present in about 1 to 10 weight percent, wherein the magnesium is present in about 10 to 30 weight percent of the complex, the manganese component is manganese ascorbate and is present in about 0.5 to 10 weight percent, wherein manganese is present in about 5 to 20 weight percent of the complex, the copper component is copper sebacate and is present in about 0.01 to 5 weight percent, wherein the copper is present in about 5 to 20 weight percent of the complex, and the carotenoid component is beta carotene and is present in about 0.1 to 5 weight percent.

In another embodiment, the pharmaceutical composition also possesses at least one of the wild yam root, wild yam extract, yellow dock, bupleurum, poria cocos, gentian root, myrrh gum, hawthorn berry extract, and rosemary extract. In a preferred embodiment, the amount of wild yam root, wild yam extract, marshmallow root, hawthorn berry extract, and rosemary extract, when present, is about 0.5 to 8 weight percent each, the amount of yellow dock, when present, is about 1 to 30 weight percent, and the amount of bupleurum, poria cocos, gentian root and myrrh, when present, is about 1 to 20 weight percent each.

The invention further relates to a method for treating and protecting skin from damage caused by the exposure to sunlight, by administering the pharmaceutical composition in a therapeutically effective amount to increase the sun protection factor of the skin. In a preferred embodiment, the composition is administered orally.

In one embodiment, the composition is administered as a tablet or capsule having about 1 mg to 2,000 mg of composition. In a preferred embodiment, the tablet or capsule has about 400 mg to 1,600 mg of composition. In a more preferred embodiment, the tablet or capsule has about 800 mg to 1,200 mg of composition.

In another embodiment, the composition is administered in conjunction with concurrent or subsequent treatment by at least one additional pharmaceutical composition used to treat or protect the skin from damage from the exposure to sunlight. In a preferred embodiment, the additional pharmaceutical composition consists of a sunscreen having at least one of the following active ingredients: titanium dioxide, zinc oxide, talc, red veterinary petrolatum, octyl methoxycinnamate, oxybenzone, octyl salicylate, and para-aminobenzoic acid; a nutritional supplement having at least one of the following: antioxidants, vitamin E, vitamin C, and carotenoids; and a a topical application having at least one of the following vitamin A, vitamin E, vitamin C, and alpha-hydroxy acids.

DETAILED DESCRIPTION OF THE PREFERRED EMBODIMENTS

A pharmaceutical formulation for advantageously protecting skin from damage caused by UV sources, such as the sun, has now been discovered. The formulation may be used alone or in conjunction with a sunscreen to provide protection from UV light. The pharmaceutical composition includes an anti-inflammatory component in an amount sufficient to reduce redness and swelling of the skin, an antioxidant is present in an amount sufficient to neutralize free radicals; and an immunity boosting component in an amount sufficient to boost the immune system to facilitate repair of UV-damaged skin. Preferably, the pharmaceutical composition optionally includes a cysteine component, magnesium component, manganese component, carotenoid component, selenium component, and copper component. Most preferably, the pharmaceutical composition also optionally includes at least one herb from the group of yellow dock, bupleurum, poria cocos, gentian root, myrrh gum, hawthorn berry extract, rosemary extract, wild yam root and wild yam extract. The synergistic effect of these pharmaceutical components boosts the sun protection factor (SPF) of known sunscreens by at least about 5 percent, preferably about 10 percent. Also, on its own the oral doses of the pharmaceutical composition provide enhanced protection of the skin against the damaging effects of the sun.

The present pharmaceutical composition advantageously protects the skin from damage resulting from exposure to UV rays, and treats such damaged skin, by providing antioxidants in the form of a catechin-based preparation such as a proanthanol or proanthocyanidin, vitamin C, vitamin A, ginkgo biloba and silymarin. These antioxidants neutralize the free radicals in the skin generated by exposure to UV light.

The pharmaceutical composition includes a vitamin C component, preferably an ascorbic acid, or a pharmaceutically acceptable salt or ester thereof, and more preferably ascorbyl palmitate, dipalmitate L-ascorbate, sodium L-ascorbate-2-sulfate, or an ascorbic salt, such as sodium, potassium, and calcium, or mixtures thereof. When oral formulations of the pharmaceutical composition are used, it is preferred that a non-acidic form of vitamin C be used to reduce the stomach irritation that may occur when using an acidic form. The vitamin C component is present in the pharmaceutical composition in about 5 to 50 weight percent, preferably about 7 to 40 weight percent, and more preferably 10 to 25 weight percent. A unit dose of the vitamin C component is typically about 50 mg to 800 mg, preferably 60 mg to 600 mg, more preferably about 80 mg to 400 mg.

The vitamin A component preferably is vitamin A palmitate present in about 5 to 50 weight percent, more preferably in about 6 to 40 weight percent, most preferably in about 7 to 30 weight percent of the composition.

The catechin-based preparation useful in the pharmaceutical composition provides powerful antioxidants to scavenge free radicals. These antioxidants provide roughly 20 times more antioxidative power than vitamin C and 50 times more antioxidative power than vitamin E. The catechin-based preparation is preferably a proanthanol or a proanthocyanidin, and more preferably a proanthanol, which is commonly obtained as a grape seed extract. The catechin-based preparation is present in about 0.1 to 5 weight percent, preferably about 0.2 to 3 weight percent, and most preferably about 0.3 to 2 weight percent of the composition. A unit dose of catechin-based preparation includes about 1 mg to 20 mg, preferably about 2 mg to 15 mg, and more preferably about 3 mg to 10 mg.

The composition preferably also includes quercetin powder. Preferably, the quercetin powder is typically quercetin dihydrate present in about 1 to 20 weight percent, preferably about 2 to 15 weight percent, and more preferably about 3 to 10 weight percent in the pharmaceutical composition. Other quercetin compounds can be used, if desired.

The silymarin component, which provides an antioxidant component that specifically targets the liver, may also be added to the pharmaceutical composition. Preferably, milk thistle extract, *Silybum marianum*, provides the silymarin for the present invention. The extract itself contains about 70 to 95 weight percent of silymarin. A unit dose of the pharmaceutical composition may include about 10 to 160 mg of the extract, preferably about 20 to 100 mg, and more preferably about 30 mg to 80 mg.

In a more preferable form, Ginkgo Biloba extract is included in the composition, as well. Volatile oils, tannin and resin are the active constituents of the extract. Ginkgo Biloba supplies antioxidants which are understood to target the brain. Ginkgo Biloba is present in about 0.01 to 3 weight percent, preferably about 0.02 to 2 weight percent, and more preferably 0.03 to 1 weight percent in the pharmaceutical composition.

The anti-inflammatory component of the composition prevents and reduces inflammation, including the redness and swelling that typically accompanies sun-damaged skin. Zinc and/or vitamin E assist in reducing the inflammation associated with overexposure to sunlight.

The zinc component of the pharmaceutical composition mitigates the inflammation associated with UV light damage and assists in binding collagen fibers within the skin. Also, zinc is essential to SOD, and thus affects the body in counteracting free radical formation. The zinc component may be any zinc compound or pharmaceutically acceptable salt thereof, but preferably is a zinc complexed with an amino acid, and more preferably is zinc monomethinone, wherein the zinc is typically present in about 10 to 30 weight percent of the complex. The zinc component is present in about 1 to 12 weight percent, preferably 1.5 to 8 weight percent, and more preferably about 2 to 6 weight percent of the pharmaceutical composition. A unit dose of the zinc source is typically about 5 to 100 mg, preferably about 10 to 75 mg, and more preferably about 15 to 60 mg. Although effective in protecting skin from sun damage, increasing the zinc concentration too much in an oral formulation of the pharmaceutical composition may lead to stomach discomfort.

The vitamin E component is preferably a sulfate or succinate vitamin E complex, and more preferably a D-alpha tocopherol acid succinate. The vitamin E component is present in about 5 to 40 weight percent, preferably about 6 to 30 weight percent, and more preferably about 7 to 20 weight percent of the composition.

An immune boosting component is also part of the composition. Immune boosters, such as echinacea and golden seal, facilitate the healing of the sun damaged tissues.

Echinacea and its extract are obtained from the Echinacea family of plants, and these components act as immune boosters. Also, they contain several potent antioxidant compounds, such as echinacoside and caffeoyl derivatives. Echinacea is present in about 1 to 20 weight percent, preferably about 2 to 15 weight percent, and more preferably about 3 to 10 weight percent of the composition.

An additional immunity boosting component is provided by the Golden Seal, *Hydrastis canaderis*, preferably present in the pharmaceutical composition. Golden Seal is present in about 1 to 20 weight percent, preferably about 2 to 15 weight percent, more preferably about 3 to 10 weight percent of the composition.

Additionally, the present invention more preferably, but optionally, contains the following: a cysteine component, a magnesium component, a manganese component, a carotenoid, a selenium component, and a copper component.

The cysteine component used in the composition is preferably N-acetyl cysteine, present in about 1 to 10 weight percent, preferably about 2 to 8 weight percent, and more preferably about 3 to 6 weight percent of the composition.

The manganese component is the co-factor used by the SOD found in mitochondria. The manganese component may be any manganese compound or pharmaceutically acceptable salt thereof, but preferably is manganese ascorbate or manganese ascorbic acid, wherein the manganese is typically present in about 5 to 20 weight percent of the complex. When complexed with vitamin C, this vitamin C source may be included in the overall percentage of vitamin C in the pharmaceutical composition.

The copper component is also preferably included in the pharmaceutical composition, and may be any copper compound or pharmaceutically acceptable salt thereof, but preferably is copper sebacate, wherein the copper is present in about 5 to 20 weight percent of the copper sebacate. The copper component is present in about 0.01 to 5 weight percent, preferably about 0.02 to 3 weight percent and more preferably about 0.03 to 2 weight percent of the composition. A unit dose of the pharmaceutical composition may include about 0.5 mg to 10 mg, preferably about 0.6 mg to 5 mg, and more preferably 0.7 mg to 3 mg.

The magnesium component may be any magnesium compound or pharmaceutically acceptable salt thereof, but more preferably is magnesium ascorbate or magnesium ascorbic acid, wherein the magnesium is typically present in about 5 to 20 weight percent of the complex. When complexed with vitamin C, this vitamin C source may be included in the overall percentage of vitamin C in the pharmaceutical composition.

Carotenoids are powerful antioxidants, and they include beta-carotene, canthaxanthin, zeaxanthin, lycopen, lutein, crocetin, and capsanthin for example. Beta carotene is a carotenoid which is predominantly found in the skin. A carotenoid component, preferably beta carotene, is present in about 0.1 to 5 weight percent, preferably 0.2 to 4 weight percent, and more preferably 0.3 to 3 weight percent in the pharmaceutical composition.

Additionally, a source of selenium may also be optionally added to the pharmaceutical composition. A selenium compound or pharmaceutically acceptable salt thereof may be used. Preferably, the selenium compound is selenium complexed with an amino acid. Most preferably, the selenium compound is L-selenomethionine, wherein the selenium is present in 0.1 to 5 weight percent of the complex. Selenomethionine is present in about 0.01 to 3 weight percent, preferably 0.05 to 2 weight percent, and more preferably at 0.1 to 1 weight percent in the pharmaceutical composition.

The pharmaceutical composition more preferably includes at lest one herb from the group of yellow dock, bupleurum, poria cocos, gentian root, myrrh gum, hawthorn berry extract, rosemary extract, wild yam root, wild yam extract, and marshmallow root.

Yellow Dock, *Rumex crispus*, is often used to treat skin disease, especially those involving some form of inflammation. The active constituents of yellow dock are rumicin and chrysarobin. Yellow Dock extract is typically present in the pharmaceutical composition in about 1 to 30 weight percent, preferably 3 to 25 weight percent, more preferably 5 to 20 weight percent.

Bupleurum, *Bupleurum falactum*, is known for its effect on the liver. The active constituents in bulpleurum are furfurol, sterol, and bupleurumol. The bupleurum is present in the present pharmaceutical composition at about 1 to 20 weight percent weight, preferably about 2 to 15 weight percent, and more preferably 3 to 10 weight percent.

The active constituents in poria cocos, *Lycoperdon solidum*, are tetracyclic titerpenic acids, polysaccharides, ergostol, choline, lipase, and protease. This herb is useful for eliminating excess fluids from the body. It is typically present in the pharmaceutical composition in about 1 to 20 weight percent, preferably about 2 to 15 weight percent, more preferably about 3 to 10 weight percent.

The bitter glycosides in gentian root, *Gentian lutea*, account for its use as a digestive bitter and liver disorder treatment. Gentian root is typically present in the pharmaceutical compositions at about 1 to 20 weight percent, preferably about 2 to 15 weight percent, more preferably about 3 to 10 weight percent.

Myrrh, *Commiphora myrrha*, has several oils, resins and gums that increase circulation and heart rate. Myrrh gum is used in the present pharmaceutical composition in about 1 to 20 weight percent, preferably about 2 to 15 weight percent, more preferably about 3 to 10 weight percent.

Hawthorn berry, *Crataegus supplement.*, can optionally be added to the pharmaceutical composition as well. This herb is useful in the treatment of heart disease. Crategolic acid, citric acid, tartaric acid, glavone, glycosides, and vitamin C are the active constituents of hawthorne berries. The hawthorn berry is typically present in about 0.5 to 8 weight percent, preferably about 0.6 to 6 weight percent, and more preferably 0.7 to 4 weight percent of the composition.

Rosemary contains aromatic oils that assist with stomach disorders, and salicylic acid. It is typically present in the pharmaceutical composition at about 0.5 to 8 weight percent, preferably about 0.6 to 6 weight percent, and more preferably about 0.7 to 4 weight percent of the composition.

Wild yam possesses glycoside saponins and diosgenins, hormonal precursors to cortical steroids that help reduce pain. It assists with problems of the liver and gall bladder, as well. It is present in the pharmaceutical composition at about 0.5 to 8 weight percent, preferably 0.6 to 6 weight percent, and more preferably about 0.7 to 4 weight percent.

The marshmallow root, *Althea officinalis*, acts as an anti-inflammatory. The mucilage in the herb soothes membranes thereby reducing inflammation. Marshmallow root is present in the pharmaceutical composition at about 0.5 to 8 weight percent, preferably about 0.6 to 6 weight percent, and more preferably about 0.7 to 4 weight percent of the composition.

The phrase "therapeutically effective amount" means the amount of the pharmaceutical composition that provides a therapeutic benefit in the protection, prevention, or treatment of skin damage resulting from exposure to UV light.

The magnitude of a prophylactic or therapeutic dose of the composition in the prevention or treatment of UV damage to skin will vary with the sensitivity of the person's skin and the route of administration. The dose, and perhaps the dose frequency, will also vary according to the age, body weight, and response of the individual patient. In general, the total daily dose range, for the conditions described herein, is from about 1 mg to about 2,000 mg administered in about one to ten doses orally. The preferred oral unit daily dose range should be from about 1 mg to 2,000 mg; more preferably about 400 mg to 1,600 mg; most preferably about 800 mg to 1,200 mg.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient's response.

Although any suitable route of administration may be employed for providing the patient with an effective dosage of the composition according to the methods of the present invention, oral administration is preferred. Suitable routes include, for example, oral, rectal, arenteral, intravenous, topical, transdermal, subcutaneous, intramuscular, and similar forms of administration may also be employed. Suitable dosage forms include tablets, troches, dispersions, suspensions, solutions, capsules, patches, suppositories, and the like, although oral dosage forms are preferred.

The pharmaceutical compositions used in the methods of the present invention include the active ingredients described above, and may also contain pharmaceutically acceptable carriers, excipients and the like, and optionally, other therapeutic ingredients. The compositions herein may also be administered in conjunction with, i.e., concurrently or sequentially, with other skin-protective pharmaceutical composition or other devices, such as a hat, umbrella and the like.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, algenic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example from N,N-dibenzylethylenediamine, chloroprocaine, choline, diethanolamine, ethylenediamine, meglumaine (N-methylglucamine), and procaine.

The compositions for use in the methods of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets and capsules.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions for use in the methods of the present invention suitable for oral administration may be presented as discrete units such as capsules, cachets, or tablets, or aerosol sprays, each containing a predetermined amount of the active ingredient, as a powder or granules, as creams, pastes, gels, or ointments, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the carrier with the active ingredient which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compressing or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet, cachet or capsule contains from about 1 mg to 2,000 mg of the active ingredient.

EXAMPLES

The invention is further defined by reference to the following examples describing in detail the preparation of the compound and the compositions used in the methods of the present invention, as well as their utility. The examples are representative, and they should not be construed to limit the scope of the invention.

Example 1: Capsules

A large number of unit capsules are prepared by filling standard two-piece hard gelatin capsules each with the desired amount of powdered active ingredient as described above, 150 milligrams of lactose, 50 milligrams of cellulose, and 6 milligrams magnesium stearate.

Example 2: Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing the desired amount of the active ingredient. The capsules are washed and dried for packaging.

Example 3: Tablets

A large number of tablets were prepared by conventional procedures so that the dosage unit included: the desired amount of active ingredient as described herein, 6 milligrams of stearic acid, 7 milligrams of sorbitol, 1.1 milligrams of magnesium stearate, and 1 milligram of syloid.

Appropriate coatings may be applied to increase palatability or delay absorption. A specific therapeutic formulation of the pharmaceutical composition described herein is set forth in the table below:

| INGREDIENTS | MG PER TABLET | PERCENT BY WEIGHT | CHEMICAL OR SCIENTIFIC NAME |
| --- | --- | --- | --- |
| Vitamin C 100% | 200.00 | 18.5% | Ascorbic acid |
| Vitamin E Succinate | 127.00 | 11.7% | D-alpha tocopheryl acid succinate |
| Yellow Dock Root | 96.00 | 8.9% | *Rumex cripus* |
| Bupleurum | 48.00 | 4.4% | *Bupleuri spp.* |
| *Poria Cocos* | 48.00 | 4.4% | *Poria cocos* |
| Echinacea | 48.00 | 4.4% | *Echinacea pallida* |
| Gentian Root | 48.00 | 4.4% | *Gentiana spp.* |
| Golden Seal | 48.00 | 4.4% | *Hydrastis canaderus* |
| Myrrh Gum | 48.00 | 4.4% | *Commiphora molmol* |
| Echinacea (extract 1.5:1) | 48.00 | 4.4% | *Echinacea angustifolium* |
| Quercetin Powder | 40.00 | 3.7% | Quercetin dihydrate |
| Milk Thistle extract (83% silymarin) | 40.00 | 3.7% | *Silybum marianum* |
| N-Acetyl Cysteine | 40.00 | 3.7% | N-acetyl cysteine |
| Opti-Zinc ® monomethionine (20%) | 30.00 | 2.8% | Zinc monomethionine |
| Magnesium Ascorbate (20%) | 30.00 | 2.8% | Magnesium ascorbate |
| Hawthorne Berry (extract 1:4) | 20.00 | 1.9% | *Crataegus spp.* |
| Rosemary (extract 5:1) | 20.00 | 1.9% | *Rosmarinus officinalis* |
| Wild Yam Root | 19.00 | 1.8% | *Dioscorea villosa* |
| Manganese Ascorbate (6.00%) | 17.00 | 1.5% | Manganese ascorbate |
| Wild Yam (extract 1-4) | 14.00 | 1.3% | *Dioscorea villosa* |
| Marshmallow Root | 14.00 | 1.3% | *Althea officinalis* |
| Beta Carotene (yields 1,250 iu per tablet) | 8.00 | 0.7% | Beta carotene |
| Grape Seed Extract | 5.00 | 0.5% | Proanthocyanidinis |
| Selenomethionine (0.50%) | 4.00 | 0.4% | L-selenomethionine |
| Vitamin A Palmitate (yields 1,250 iu per tablet) | 4.00 | 0.4% | Vitamin A palmitate |
| Copper Sebacate (14.00%) | 1.10 | 0.1% | Copper Sebacate |
| Ginkgo Biloba Extract 50:1 | 1.00 | 0.1% | Ginkgo biloba |

These tablets are an example of a preferred embodiment of a unit dose according to the present invention.

Examples 4–6: Effectiveness of Skin-protectiveness Composition Against UV-Damage Three separate tests were conducted to evaluate the potential of the present invention to change the photobiological responsiveness of the skin in human subjects. Each of the tests first evaluated the SPF of a sunscreen prior to using the present invention, and then evaluated the SPF of the sunscreen in conjunction with the present invention. The three sunscreens used in the tests were MURASUN® Hand, Neck, and Decollete Sunscreen, MURASUN® Daily Sunscreen, and MURASUN® Daily Sunblock available from Murad, Inc., El Segundo, Calif. Also, the formulation used in example 3 was used for the vitamin supplements administered.

In each of the tests, ten volunteers between the ages of 18 and 60 were selected having fair skin of types I–III, determined by the following guidelines:

a) 18 to 60 years of age;

b) Fair skinned with skintypes I–III, where:

I always burns easily; never tans (sensitive)

II always burns easily; tans minimally (sensitive)

III burns moderately; tans gradually (normal)

IV burns minimally; always tans well (normal)

V rarely burns; tans profusely (insensitive)

VI never burns; deeply pigmented (insensitive)

These panelists were first subjected to a determination of the pre-antioxidant vitamin supplement static sun protection factor (SPF) values. A sufficient number of 5×10 cm test site areas were outlined with a surgical marking pen on each subject's back between the scapulae and the beltline, lateral to the midline. These areas were designated for the Test Material and Standard, with an adjacent site designated for a concurrent Minimal Erythemal Dose (MED).

The MED is defined as the time interval or dosage of UV light irradiation sufficient to produce a minimal, perceptible erythema on designated test sites. Prior to the testing phase, the MED of the unprotected skin of each subject was determined by a progressive sequence of timed UV light exposures, graduated incrementally by 25 percent over the previous exposure. Sixteen to twenty-four hours after irradiation, the sites were evaluated for erythema according to the following scoring system:

0=Negative, no visible reaction

±=Minimal erythema

1+=Defined erythema

2+=Moderate erythema

3+=Severe erythema

A 0.1 ml or 0.1 g portion of the Test Material and of the Standard was applied to the appropriate designated test site and spread evenly over the site using a finger cot. After product application, each test area was subdivided into sites which were used for defined serial UV light exposure. A Xenon Arc Solar Simulator, commercially available from the Solar Light Company, Philadelphia, Pa., was used as the source of ultraviolet light. A continuous emission spectrum in the UV-B range (290–320 nanometers) was produced during the testing procedure by this instrument. Irradiation of the sites was begun no less than 15 minutes and no longer than 30 minutes after application.

Exposure times were selected for each site in treated areas based upon the previously determined MED of the unprotected skin and the expected SPF of the test material or the standard.

All test sites were evaluated 16 to 24 hours after irradiation to determine the minimal erythemal response.

Next a determination of the post-antioxidant vitamin supplement SPF values was made using the vitamin supplement formulation provided in Example 3.

Each of the volunteers was provided with the vitamin supplement tablets of the present invention with instructions to take the tablets twice daily.

The sites were outlined on the subject's back and the sunscreen application, waiting period and irradiation procedure, previously described, was followed. All test sites were evaluated 16 to 24 hours after irradiation to determine minimal erythemal responses.

The SPF for the Test Material and Standard for each subject was calculated according to the formula:

SPF=MED Test Material or Standard/MED Unprotected Control

The test results and conclusions for the three tests are presented below.

Example 4: MURASUN® Hand, Neck and Decollete Sunscreen

Example 4 was performed using MURASUN® Hand, Neck and Decollete Sunscreen. The MURASUN® Hand, Neck and Decollete Sunscreen has the following formulation:

MURAD
FORMULA FOR HAND, NECK & DECOLLETE HYDRATING CREAM SPF-15

Percentage Formula

| Name Of Ingredient | % By Weight |
|---|---|
| 1. Water (Aqua) | 58.46% |
| 2. Octyl Methoxycinnamate | 7.5 |
| 3. Glycolic Acid | 5.6 |
| 4. Glycerin | 5.00 |
| 5. Oxybenzone | 4.00 |
| 6. Butylene Glycol | 4.00 |
| 7. Sodium Hydroxide | 2.00 |
| 8. DEA-Cetyl Phosphate | 1.80 |
| 9. Glyceryl Stearate | 1.5 |
| 10. PEG-100 Stearate | 1.50 |
| 11. Magnesium Aluminum Silicate | 1.30 |
| 12. Cetearyl Alcohol | 1.00 |
| 13. Ceteareth-20 | 1.00 |
| 14. Dimethicone | 1.00 |
| 15. Calcium Sodium Borosilicate | 1.00 |
| 16. Keratin Amino Acids | 0.10 |
| 17. $C_{12-13}$ Alkyl Lactate | 0.50 |
| 18. Lecithin | 0.01 |
| 19. Tocopherol | 0.01 |
| 20. Magnesium Ascorbyl Phosphate | 0.01 |
| 21. Retinyl Palmitate | 0.01 |
| 22. Corn (Zea Mays) Oil | 0.01 |
| 23. Lemon (Citrus Medica Limonum) Peel Extract | 0.10 |
| 24. Propylene Glycol | 0.40 |
| 25. Sodium PCA | 0.50 |
| 26. Panthenol | 0.40 |
| 27. allantoin | 0.10 |
| 28. Xanthan Gum | 0.50 |
| 29. Disodium EDTA | 0.10 |
| 30. Diazolidinyl Urea | 0.30 |
| 31. Methylparaben | 0.15 |
| 32. Butylparaben | 0.06 |
| 33. Ethylparaben | 0.05 |
| 34. Propylparaben | 0.03 |
| | 100.00% |

The SPF calculations obtained for each panelist regarding MURASUN® Hand, Neck and Decollete Sunscreen alone and MURASUN® Hand, Neck and Decollete Sunscreen with the present invention are represented in table 1. No adverse dermal irritations were observed on the treated area of any panelist.

Under the conditions of this study, the pre-antioxidant vitamin supplement (static) average Sun Protection Factor of MURASUN® Hand, Neck and Decollete Sunscreen was calculated to be 15.7.

Following the oral treatment, the post-antioxidant vitamin supplement Sun Protection Factor was calculated to be 16.1.

The test concluded that there was a 2.5% increase in the mean SPF value of the test sunscreen product following one week of twice daily ingestion of an antioxidant vitamin supplement.

TABLE 1

SPF Results for MURASUN ® Hand, Neck and Decollete Sunscreen Used Alone and With Vitamin Supplement

| Subject | Skin Type | Murasun ® Hand, Neck and Decollete Pre-Antioxidant Vitamin Supplement | Murasun ® Hand, Neck and Decollete Post-Antioxidant Vitamin Supplement |
|---|---|---|---|
| 1) | II | 15.0 | 18.7 |
| 2) | II | 15.0 | 18.7 |
| 3) | II | 15.0 | 15.0 |
| 4) | II | 15.0 | 15.0 |
| 5) | II | 15.0 | 15.0 |
| 6) | II | 15.0 | 15.0 |
| 7) | II | 18.7 | 18.7 |
| 8) | II | 18.7 | 15.0 |
| 9) | II | 15.0 | 15.0 |
| 10) | II | 15.0 | 15.0 |
| | | 15.7 | 16.1 |

Example 5: MURASUN® Daily Sunscreen

Example 5 was performed using MURASUN® Daily Sunscreen. The MURASUN® Daily Sunscreen has the following formulation:

MURAD

FORMULA FOR MURASUM DAILY SUNSCREEN SPF-15

Percentage Formula

| Name of Ingredient | % by Weight |
|---|---|
| 1. Water (Aqua) | 61.27% |
| 2. Octyl Methoxycinnamate | 7.5 |
| 3. Dicaprylyl Maleate | 5.00 |
| 4. Octyl Salicylate | 5.00 |
| 5. Oxybenzone | 4.00 |
| 6. Glycerin | 5.00 |
| 7. Stearic Acid | 3.00 |
| 8. PVP/Eicosene Copolymer | 3.00 |
| 9. DEA-Cetyl Phosphate | 2.00 |
| 10. Cetyl Alcohol | 1.00 |
| 11. Dimethicone | 0.20 |
| 12. Lecithin | 0.01 |
| 13. Tocopherol | 0.01 |
| 14. Magnesium Ascorbyl Phosphate | 0.01 |
| 15. Lemon (Citrus Medica Limonum) Peel Extract | 0.10 |
| 16. Propylene Glycol | 0.40 |
| 17. Melanin | 0.01 |
| 18. Glycolipids | 0.10 |
| 19. Hyaluronic Acid | 0.10 |
| 20. Sodium PCA | 0.50 |

-continued

| Name of Ingredient | % by Weight |
|---|---|
| 21. Carbomer | 0.23 |
| 22. Triethanolamine | 0.41 |
| 23. Disodium EDTA | 0.05 |
| 24. Diazolidinyl Urea | 0.30 |
| 25. Methylparaben | 0.20 |
| 26. Propylparaben | 0.10 |
| 27. Titanium Dioxide | 0.50 |
|  | 100.00% |

The SPF calculations obtained for each panelist regarding the SPF of MURASUN® Daily Sunscreen alone and MURASUN® Daily Sunscreen with the present invention are represented in Table 2. No adverse dermal irritations were observed on the treated area of any panelist.

Under the conditions of this study, the pre-antioxidant vitamin supplement (static) average Sun Protection Factor of Murasun® Daily Sunscreen was calculated to be 17.98.

Following the oral treatment, the post-antioxidant vitamin supplement Sun Protection Factor was calculated to be 19.84.

The test concluded that there was a 10.34% increase in the mean SPF value of the test sunscreen product following one week of twice daily ingestions of an antioxidant vitamin supplement.

TABLE 2

SPF Results for MURASUN ® Daily Sunscreen Used Alone and With Vitamin Supplement

| Subject | Skin Type | Murasun ® Daily Sunscreen Pre-Antioxidant Vitamin Supplement | Murasun ® Daily Sunscreen Post-Antioxidant Vitamin Supplement |
|---|---|---|---|
| 1) | II | 15.0 | 18.7 |
| 2) | II | 18.7 | 23.4 |
| 3) | II | 18.7 | 18.7 |
| 4) | II | 18.8 | 23.4 |
| 5) | II | 18.7 | 18.7 |
| 6) | II | 18.7 | 23.4 |
| 7) | II | 18.7 | 18.7 |
| 8) | II | 15.0 | 15.0 |
| 9) | II | 18.7 | 23.4 |
| 10) | II | 18.8 | 15.0 |
|  |  | 17.98 | 19.84 |

Example 6: MURASUN® Daily Sunblock

Example 6 was performed using MURASUN® Daily Sunblock. The MURASUN® Daily Sunblock has the following formulation:

MURAD

FORMULA FOR MURASUN DAILY SUNBLOCK SPF-15

Percentage Formula

| Name of Ingredient | % by Weight |
|---|---|
| 1. Water (Aqua) | 68.55% |
| 2. Propylene Glycol Dicaprylate/Dicaprate | 10.00 |
| 3. Butylene Glycol | 6.00 |
| 4. Titanium Dioxide | 5.60 |

-continued

| Name of Ingredient | % by Weight |
|---|---|
| 5. Isodecyl Neopentanoate | 3.00 |
| 6. Cetyl Alcohol | 2.00 |
| 7. Glyceryl Stearate | 1.25 |
| 8. PEG-100 Stearate | 1.25 |
| 9. Potassium Cetyl Phosphate | 0.10 |
| 10. Lecithin | 0.01 |
| 11. Tocopherol | 0.01 |
| 12. Magnesium Ascorbyl Phosphate | 0.01 |
| 13. Sodium PCA | 0.10 |
| 14. Polyisoprene | 0.03 |
| 15. Soybean (Glycine Soja) Sterol | 0.02 |
| 16. Retinyl Palmitate | 0.01 |
| 17. Ascorbyl Palmitate | 0.01 |
| 18. Lemon (Citrus Medica Limonum) Peel Extract | 0.10 |
| 19. Propylene Glycol | 0.40 |
| 20. Xanthan Gum | 0.25 |
| 21. Carbomer | 0.25 |
| 22. Triethanolamine | 0.30 |
| 23. Disodium EDTA | 0.10 |
| 24. Diazolidinyl Urea | 0.30 |
| 25. Methylparaben | 0.25 |
| 26. Propylparaben | 0.10 |
|  | 100.00% |

The SPF calculations obtained for each panelist regarding the SPF of MURASUN® Daily Sunblock alone and with the vitamin supplement are represented in Table 3. No adverse dermal irritations were observed on the treated area of any panelist.

Under the conditions of this study, the pre-antioxidant vitamin supplement (static) average Sun Protection Factor of Murasun® Daily Sunblock was calculated to be 17.24.

Following the oral treatment, the post-antioxidant vitamin supplement Sun Protection Factor was calculated to be 18.63.

This test concluded that there was a 7.9% increase in the mean SPF value of the test sunscreen product following one week of twice daily ingestion of an antioxidant vitamin supplement.

TABLE 3

SPF Results for MURASUN ® Daily Sunblock Used Alone and With Vitamin Supplement

| Subject | Skin Type | Murasun ® Daily Sunblock Pre-Antioxidant Vitamin Supplement | Murasun ® Daily Sunblock Post-Antioxidant Vitamin Supplement |
|---|---|---|---|
| 1) | II | 18.7 | 18.7 |
| 2) | II | 18.7 | 18.7 |
| 3) | II | 15.0 | 23.4 |
| 4) | II | 18.8 | 23.4 |
| 5) | II | 18.7 | 18.7 |
| 6) | II | 15.0 | 15.0 |
| 7) | II | 18.7 | 15.0 |
| 8) | II | 15.0 | 15.0 |
| 9) | II | 15.0 | 23.4 |
| 10) | II | 18.8 | 15.0 |
|  |  | 17.24 | 18.63 |

Although preferred embodiments of the invention have been described in the foregoing Detailed Description of the Invention, it will be understood that the invention is not limited to the embodiments disclosed but is capable of numerous modifications without departing from the spirit and scope of the present invention. It will be understood that the chemical details may be slightly different or modified by one of ordinary skill in the art without departing from the methods and compositions disclosed and taught by the present invention.

What is claimed is:

1. A pharmaceutical composition for the protection from or treatment of skin damage resulting from exposure to skin damaging light in a patient comprising:
   at least one primary antioxidant component in an amount sufficient to reduce free radicals in the patient's body;
   at least one anti-inflammatory component in an amount sufficient to reduce inflammation of the patient's skin; and
   at least one immunity boosting component in an amount sufficient to stimulate the patient's immune system response to protect skin or facilitate repair of damaged skin.

2. The pharmaceutical composition of claim 1, wherein the primary antioxidant component is present in about 5 to 50 weight percent, the anti-inflammatory component is present in about 5 to 40 weight percent, and the immunity boosting component is present in about 1 to 20 weight percent of the composition.

3. The pharmaceutical composition of claim 1, wherein the primary antioxidant component comprises at least one of a catechin-based preparation, a vitamin A source, a ginko biloba extract, a silymarin source, a quercetin compound, or a vitamin C source.

4. The pharmaceutical composition of claim 3, wherein the catechin-based preparation is a proanthanol or proanthocyanidin, the vitamin A source is vitamin A palmitate, the silymarin source is milk thistle extract, the quercitin compound is quercitin dihydrate, and the vitamin C source is an ascorbic acid compound, or a salt or ester thereof.

5. The pharmaceutical composition of claim 4, wherein the primary antioxidant component comprises proanthocyanidin present in about 0.1 to 5 weight percent, vitamin A palmitate present in about 0.1 to 5 weight percent, ginkgo biloba extract present in about 0.01 to 3 weight percent, the quercetin dihydrate and is present in about 1 to 20 weight percent, ascorbic acid present in about 5 to 50 weight percent, and milk thistle extract present in about 1 to 20 weight percent.

6. The pharmaceutical composition of claim 1, wherein the anti-inflammatory component comprises a vitamin E source, a zinc compound or a pharmaceutically acceptable salt thereof.

7. The pharmaceutical composition of claim 6, wherein the vitamin E source is a sulfate or succinate complex of vitamin E and the zinc compound is a complex of zinc and an amino acid.

8. The pharmaceutical composition of claim 7, wherein the vitamin E source is D-alpha tocopherol acid succinate present in about 5 to 40 weight percent, and the zinc compound is zinc monomethinone present in about 1 to 12 weight percent, wherein the zinc is preferably present in about 10 to 30 weight percent of the complex.

9. The pharmaceutical composition of claim 1, wherein the immunity boosting component comprises at least one of echinacea, an echinachea extract, or golden seal.

10. The pharmaceutical composition of claim 1, wherein the composition further comprises a pharmaceutically acceptable carrier or excipient.

11. The pharmaceutical composition of claim 1, further comprising one or more of a cysteine component, a magnesium component, manganese component, a copper component, a selenium component, or a carotenoid component.

12. The pharmaceutical composition of claim 11, wherein the cysteine component is N-acetyl cysteine and is present in about 1 to 10 weight percent, the magnesium component is magnesium ascorbate and is present in about 1 to 10 weight percent, wherein the magnesium is present in about 10 to 30 weight percent of the complex, the manganese component is manganese ascorbate and is present in about 0.5 to 10 weight percent, wherein manganese is present in about 5 to 20 weight percent of the complex, the copper component is copper sebacate and is present in about 0.01 to 5 weight percent, wherein the copper is present in about 5 to 20 weight percent of the complex, and the carotenoid component is beta carotene and is present in about 0.1 to 5 weight percent.

13. The pharmaceutical composition of claim 11, further comprising at least one of the wild yam root, wild yam extract, yellow dock, bupleurum, poria cocos, gentian root, myrrh gum, hawthorn berry extract, or rosemary extract.

14. The pharmaceutical composition of claim 13, wherein the amount of wild yam root, wild yam extract, marshmallow root, hawthorn berry extract, and rosemary extract, when present, is about 0.5 to 8 weight percent each, the amount of yellow dock, when present, is about 1 to 30 weight percent, and the amount of bupleurum, poria cocos, gentian root and myrrh, when present, is about 1 to 20 weight percent each.

15. A method for treating and protecting skin from damage caused by the exposure to sunlight, which comprises administering the pharmaceutical composition of claim 1 in therapeutically effective to increase the sun protection factor of the skin.

16. The method of claim 15, wherein the composition is administered orally.

17. The method of claim 16, wherein the composition is administered as a tablet or capsule having about 1 mg to 2,000 mg of composition.

18. The method of claim 17, wherein the tablet or capsule has about 400 mg to 1,600 mg of composition.

19. The method of claim 18, wherein the tablet or capsule has about 800 mg to 1,200 mg of composition.

20. The method of claim 15, which further comprises concurrently or subsequently administering at least one additional pharmaceutical composition comprising a sunscreen, a nutritional supplement or a topical application used to treat or protect the skin from damage from the exposure to skin damaging light.

21. The method of claim 20, wherein the additional pharmaceutical composition comprises:
   a sunscreen having at least one of the following active ingredients: titanium dioxide, zinc oxide, talc, red veterinary petrolatum, octyl methoxycinnamate, oxybenzone, octyl salicylate, or para-aminobenzoic acid;
   a nutritional supplement having at least one of the following: antioxidants, vitamin E, vitamin C, or carotenoids; or
   a topical application having at least one of the following: vitamin A, vitamin E, vitamin C, or alpha-hydroxy acids.

* * * * *